United States Patent [19]
Kevan et al.

[11] Patent Number: 5,631,024
[45] Date of Patent: May 20, 1997

[54] MEDICAMENTS FOR BENEFICIAL INSECTS AND METHOD

[75] Inventors: Sherrene D. Kevan; Peter G. Kevan, both of Cambridge, Canada; Jack D. Trevino, San Antonio, Tex.

[73] Assignee: Enviroquest, Ltd., Canada

[21] Appl. No.: 445,705

[22] Filed: May 22, 1995

[51] Int. Cl.$^6$ ............................................ A01N 25/28
[52] U.S. Cl. ..................... 424/486; 424/405; 424/408; 424/489
[58] Field of Search ................ 514/729; 424/489, 424/486, 490, 408, 405

[56] References Cited

U.S. PATENT DOCUMENTS

| | | | |
|---|---|---|---|
| 4,316,884 | 2/1982 | Alam et al. | 424/495 |
| 4,720,423 | 1/1988 | Fraser | 428/313.5 |
| 5,000,198 | 3/1991 | Nakajima | 131/331 |
| 5,286,496 | 2/1994 | Stapler et al. | 424/490 |
| 5,300,290 | 4/1994 | Spencer | 424/490 |

FOREIGN PATENT DOCUMENTS

| | | |
|---|---|---|
| 1110972 | 3/1978 | Canada . |
| 1292429 | 10/1986 | Canada . |
| 3427330 | 7/1984 | Germany . |
| 230752 | 12/1985 | Germany . |
| 3914496 | 5/1989 | Germany . |
| 2078613 | 9/1988 | Japan . |

*Primary Examiner*—Thurman K. Page
*Assistant Examiner*—William E. Benston, Jr.
*Attorney, Agent, or Firm*—John L. Sigalos

[57] ABSTRACT

There are disclosed therapeutic microcapsules for beneficial insects having a non-toxic matrix with a medicament for treating a beneficial insect disorder substantially uniformly distributed therethrough and therapeutic compositions in which the microcapsules are in a carrier. Also disclosed is the method of treating beneficial insect disorders with such microcapsules and compositions.

13 Claims, No Drawings

MEDICAMENTS FOR BENEFICIAL INSECTS AND METHOD

BACKGROUND OF THE INVENTION

The present invention relates to ingestible therapeutic compositions for beneficial insects and to the method of treating disorders of beneficial insects.

There are a number of disorders that affect beneficial insects with an example being controlling parasitic and/or pathogenic infestations in bees, particularly honeybees. It is known, for example, that certain mites affect and destroy entire colonies. Other organisms (parasites, fungi, bacteria, viruses, and the like) cause *Nosema* disease, chalk brood disease, sac-brood disease, American and European foul-brood diseases, and the like. Certain of such disorders also affect other useful bees, such as alfalfa leafcutting bees (*Megachile rotundata*), orchard bees (*Osmia* species), and bumblebees (*Bombus* species) used in commercial production.

Other beneficial insects used for commercial or scientific purposes, such as silkworms, are also affected by parasites and microorganisms. Insects and arthropods kept in culture for commercial or scientific research are susceptible to similar diseases and nematode worm parasites.

In order to treat such disorders, a number of techniques are utilized. Referring to treatment of mite infestation in bees, it has been known to use a variety of chemicals to fumigate the bee colonies, or to place certain other compounds therein to try to eliminate the mites from the hive where the colony resides. Among such materials are menthol, formic acid, bromopropylate, Coumaphos, pyrethrum extracts (both naturally occurring and synthetic types) and the like.

While generally useful, all of these compositions and techniques are not effective for a variety of reasons. One of the problems is that certain of these compounds, such as menthol and formic acid, when placed in the hive adversely affect the behavior of the bees. Because of their strong odor, the bees have an aversion to them and make every effort to remove them from the hive. With other compounds the bees must be removed from the hive, the hive treated, and the bee colony then returned after a period of several weeks. This is a costly and time-consuming process. Also, formic acid is corrosive and difficult and dangerous to handle. Moreover, certain of these compounds are only effective in warm weather conditions. This is particularly true with menthol, which requires at least two weeks of warm weather to cause it to vaporize in order to be effective. In many areas of the world this is a condition that does not exist throughout the year and, thus, is not effective.

Moreover, with certain miticides it is difficult to cause the bees to ingest the same and this is particularly a problem in trying to treat tracheal mites residing in the trachea of the bees. If they cannot ingest the miticide to place it into their hemolymph, then the miticide will not be effective.

These same types of problems are present with other bee and other beneficial insect disorder treatments. Chemical insecticides when used, as in treating parasitic wasps affecting alfalfa leafcutting bees, have to be used in levels that can adversely affect the bees. These adverse effects include aversion to feeding; memory loss; reduced growth, longevity, and fecundity; and temporary to chronic aberrancies in behavior. Silkworms are treated in commercial rearing operations with antifungal agents and antibacterial agents, as are many insects used for biological control and integrated pest management to prevent the cultures from dying out. In addition to possible aversion to the treatment agent, there is also the problem of the need of high levels of usage which can have adverse effects on the beneficial insect. Here again, there is the need to ensure insect intake of the treatment agent, while at the same time minimizing the amount of agent used to minimize, and preferably eliminate, possible adverse effects.

There is, thus, the need to have a composition that can be effective all year round with regard to temperature, that will ensure that the medicament can be ingested by the insect, and above all it must be a cost effective means of controlling the disorder to make it economically feasible for use. In the case of honeybees, there is the further need to ensure that the treatment will not result in unacceptable levels of toxic chemicals in the hive products such as honey, beeswax, pollen, propolis, venom, and the like.

SUMMARY OF THE INVENTION

The present invention provides a composition and method for effective and efficient treatment of beneficial insect disorders, avoiding aversion by the insects, avoiding the need for vaporization and enabling year round administration, and which will be readily ingested by the insects.

Briefly stated, the present invention comprises a carrier having microcapsules substantially uniformly distributed therethrough, said microcapsules comprising a non-toxic matrix having substantially uniformly distributed therein a medicament for treating a beneficial insect disorder.

The invention also comprises the microcapsules and the method of treating beneficial insect disorders as hereinafter described.

DETAILED DESCRIPTION

As used herein, the term "beneficial insects" is used to denote insects having commercial and/or scientific value, as in the production of food and other products (honey, silk, beeswax, etc.), pollination of agricultural crops, and entomological studies to control insect infestations. While the instant invention is applicable to a wide range of beneficial insect disorders, as has been discussed above, it will be described primarily with respect to mite infestations of bees used for agricultural purposes. Such use includes honeybees, as well as other bees that are used to pollinate many agricultural crops. Particular emphasis will be placed on tracheal mites because they are exceedingly deadly.

The instant invention permits ingestion of the material used to treat the mites so that it becomes included in the hemolymph and thus toxic to the tracheal mites. This is particularly necessary in treating tracheal mites, because such mites tend to pierce the trachea of the bee and feed on the hemolymph. If the substance that is toxic to them is present in the hemolymph, it will, of course, destroy the mites and thus preserve the life of the bee and of the colony.

An essential aspect of the instant invention is the preparation of microcapsules. As used herein, the term "microcapsules" is also intended to include microspheres. The microspheres are formed of a matrix having distributed therethrough at least one medicament effective to treat the disorder and the microcapsules are formed by placing a shell about the microspheres.

In the instant case there are a number of medicaments for treating the parasites as has been noted above and any of these can be utilized for mite infections in bees. It is preferred to utilize menthol. Menthol is available in crystalline, liquid, or granular form. Any of these are suitable in the microcapsules of the instant invention, although it is preferred to use food-grade menthol crystals.

As will be evident, the amount of menthol included in the microcapsule can vary widely, depending upon the effective amount desired to be utilized with any particular insect. Ordinarily, the microcapsules can contain anywhere from 10 to 50% by weight or more of the menthol crystals. Other medicaments are added in the amounts required for effectiveness, which for any microcapsule system and disorder can be determined by routine experimentation.

With respect to the matrix, any non-toxic material can be utilized, including food-grade fats, such as stearic acid and food-grade polymers, such as the hydroxyalkyl celluloses, (examples being hydroxymethylcellulose, hydroxyethylcellulose, hydroxypropylcellulose, and the like), polyamides, gelatin, zein and the like, or combinations thereof. Any fats or polymers that are food-grade and known for use in microencapsulation can be used, provided they are not toxic to the insect. For any given medicament, the optimum matrix material can be determined by routine experimentation.

If desired, attractants such as sugar; pollen; floral, vegetable and fruit scents; natural and synthetic pheromone; mixtures thereof; and the like can be included in the matrix to attract the bees to ingest the microcapsules. Alternatively, such attractants as it is possible to incorporate may be added to the shell-forming material used to form a shell about the microspheres or to both.

Although the microcapsules can be used as such by placing them in a hive, it is preferred to use a non-toxic carrier for the microencapsulated medicament and such carrier can either be a solid or liquid and is any material that is or can be used as a food for bees. The solid carrier can be what is termed in beekeeping as "cake" or "candy", which is an icing sugar in which the microencapsulated menthol, for example, can be substantially uniformly distributed. Also suitable are a number of commercially available patties which are, in effect, substitute pollen into which the microencapsulated menthol can be added. Equally suitable are the use of granular or powdered sugar and pollen or pollen-like powdery materials to which the microcapsules can be added. The microcapsules also can be added into liquid mixtures such as sugar syrups, honeys, and the like. It will be evident that for use in liquid carriers, the microspheres are formed of a water-insoluble matrix, such as a food-grade fat, particularly stearic acid. The amount added can vary widely, depending upon the dosage desired to be given to the bee.

When ingested by the bees, the microcapsules are disrupted by the pressure and enzymatic action of the bees' digestive system to permit the menthol to diffuse through the wall of the gut and enter the hemolymph where it will be effective to prevent the destructive effects of the tracheal mites.

The method of forming the microcapsules does not form a part of the instant invention and any of the techniques conventionally used for this purpose can be utilized. One suitable method is the utilization of a rotating disk device consisting of high speed rotating disks positioned above a collection area. By way of example, the menthol crystals are dispersed in a solution of stearic acid, a matrix material such as a hydroxyalkyl cellulose, gelatin, or mixture thereof and fed to the center of a rotating disk. The mixture fed to the center of the rotating disk spreads into a thin film and breaks up into the desired particle size at the periphery of the disk.

The resultant droplets are solidified by collecting in a cold zone, which causes the polymer or stearic acid to solidify. The encapsulated menthol crystals are entrapped within this polymer matrix.

It is well known and conventional that depending upon the speed of the disk and other factors, that the particle size of the microspheres can be varied. In the instant application it is desirable to have a particle sizing of the microcapsules about 40 to 120 microns.

If desired, a shell can be placed about the microspheres to form microcapsules. Such shell material can be any conventionally used to form microcapsule shells such as a hydroxyalkylcellulose and zein.

To form the microcapsules the microspheres are substantially uniformly distributed in a solution of the shell-forming material and such mixture fed to the center of a disk-type encapsulator, as discussed above, or other conventional encapsulating device, to form the shell about the microspheres.

It is, as previously noted, necessary to have non-toxic, preferably food grade materials to form the microcapsules to ensure that the bees are not adversely affected.

The amount of microcapsules added to any of the carriers can vary widely, as has been noted.

The invention will be further described in connection with the following examples which are set forth for purposes of illustration only.

EXAMPLES 1 TO 9

Set forth below in Table 1 is a listing of the microsphere and microcapsule compositions setting forth in percentage by weight the components of the matrix and of the menthol crystals. The table also sets forth the size range of the microspheres and microcapsules formed and the theoretical payload of the menthol crystals.

The microspheres were formed by admixing the components with the matrix in fluid form, the mixture fed to the rotating disk, and the resultant droplets solidified by cooling.

The microcapsules were formed by substantially uniformly dispersing 75 wt. % of the microspheres in a 10% zein solution (80% by wt. ethyl alcohol and 20% by wt. water) and forming the microcapsules on a conventional rotating disk device.

TABLE I

| Example | | | Composition | Payload | Size Range |
|---|---|---|---|---|---|
| 1. | | | 55% Stearic Acid<br>5% Sugar<br>40% Menthol Crystals | 40% | ~25–100 |
| 2. | a) | Core | 75% Microspheres of Ex. 1 | 30% | ~30–110 |
|   | | Shell | 25% Zein | | |
| 3. | | | 75% Stearic Acid<br>5% Sugar<br>20% Menthol Crystals | 20% | ~15–120 |
| 4. | a) | Core | 75% Microspheres of Ex. 3 | 15% | ~30–120 |
|   | b) | Shell | 25% Zein | | |
| 5. | | | 85% Stearic Acid<br>5% Sugar<br>10% Menthol Crystals | | ~10–95 |
| 6. | a) | Core | 75% Microspheres of Ex. 5 | 7.5% | ~30–120 |
|   | b) | Shell | 25% Zein | | |
| 7. | | | 50% Hydroxypropyl cellulose | 50% | ~5–20 |

TABLE I-continued

| Example | Composition | Payload | Size Range |
|---|---|---|---|
| 8. | 50% Menthol Crystals<br>35% Hydroxypropyl cellulose<br>35% Gelatin<br>5% Sugar<br>25% Menthol Crystals | 25% | ~5–25 |
| 9. | 40% Polyamide Resin<br>24% Hydroxypropyl cellulose<br>4% Sorbitol<br>32% Menthol Crystals | 32% | ~5–25 |

These microspheres were then tested and it was found that there was minimal odor of menthol from the microspheres and essentially no menthol odor from the microcapsules. This eliminates the problem of aversion of bees to ingesting the menthol in this form. It has been found that the encapsulated menthol, when in sugar candy and syrup, provides strong and effective doses of menthol to the bees' hemolymph.

It will be evident that more than one medicament can be included in the microcapsules, with more than one in the matrix or with at least one in the matrix and at least one in the shell. Also, medicaments for various disorders can be included in the same microcapsule or microcapsules containing different medicaments can first be prepared and then admixed to be ingested by the insect(s).

While the invention has been described in connection with a preferred embodiment, it is not intended to limit the scope of the invention to the particular form set forth, but on the contrary, it is intended to cover such alternatives, modifications, and equivalents as may be included within the spirit and scope of the invention as defined by the appended claims.

What is claimed is:

1. An ingestible therapeutic microcapsule for bees comprising a non-toxic matrix comprising a food grade fat, food grade polymer, or mixtures thereof having substantially uniformly distributed therein a miticide.

2. The microcapsule of claim 1 wherein the insect is a honeybee and the miticide is menthol.

3. The microcapsule of claim 2 wherein the matrix is a food-grade fat containing from about 10 to 50% by weight menthol crystals.

4. A therapeutic composition for ingestion by a bee comprising a carrier having microcapsules substantially uniformly distributed therethrough, said microcapsules comprising a non-toxic matrix comprising a food grade fat, food grade polymer, or mixtures thereof having substantially uniformly distributed therein a miticide.

5. The therapeutic composition of claim 4 wherein the insect is a honeybee, the carrier is a cake, candy, pollen or substitute pollen, granular or powdered sugar, sugar syrups, honeys, or mixture thereof, and the miticide is menthol.

6. The therapeutic composition of claim 5 wherein the matrix is a food-grade fat containing from about 10 to 50% by weight menthol crystals.

7. A method of treating a mite infestation of a bee comprising placing in a location frequented by said bee an ingestible composition comprising microcapsules comprising a non-toxic matrix comprising a food grade fat, food grade polymer, or mixtures thereof having substantially uniformly distributed therein a miticide.

8. The method of claim 7 wherein the insect is a honeybee and the miticide is menthol.

9. The method of claim 7 wherein the matrix is a food-grade fat containing from about 10 to 50% by weight menthol crystals.

10. The method of claim 7 wherein the composition includes a carrier.

11. The method of claim 10 wherein the carrier is a material used as a food for bees.

12. The method of claim 11 wherein the insect is a honeybee, the carrier is a cake, candy, pollen or substitute pollen, granular or powdered sugar, sugar syrups, honeys, or mixture thereof.

13. The method of claim 12 wherein the matrix is a food-grade fat containing from about 10 to 50% by weight menthol crystals.

* * * * *